(12) United States Patent
Tepe et al.

(10) Patent No.: US 11,358,942 B2
(45) Date of Patent: Jun. 14, 2022

(54) SUBSTITUTED PHENOTHIAZINES AS PROTEASOME ACTIVATORS

(71) Applicant: Board of Trustees of Michigan State University, East Lansing, MI (US)

(72) Inventors: Jetze J. Tepe, East Lansing, MI (US); Theresa A. Lansdell, East Lansing, MI (US); Evert Njomen, Ypsilanti, MI (US); Corey Lee Jones, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/619,876

(22) PCT Filed: Jun. 4, 2018

(86) PCT No.: PCT/US2018/035869
§ 371 (c)(1),
(2) Date: Dec. 5, 2019

(87) PCT Pub. No.: WO2018/226589
PCT Pub. Date: Dec. 13, 2018

(65) Prior Publication Data
US 2020/0165216 A1 May 28, 2020

Related U.S. Application Data

(60) Provisional application No. 62/515,403, filed on Jun. 5, 2017.

(51) Int. Cl.
*A61K 31/5415* (2006.01)
*C07D 417/14* (2006.01)
*C07D 279/22* (2006.01)
*C07D 417/06* (2006.01)

(52) U.S. Cl.
CPC ......... *C07D 279/22* (2013.01); *C07D 417/06* (2013.01)

(58) Field of Classification Search
CPC .. C07D 417/06; C07D 223/22; C07D 279/14; C07D 279/22; C07D 279/36; C07D 417/14; A61P 35/00; A61K 31/5415
USPC ................. 514/225, 224.8; 549/15
See application file for complete search history.

(56) References Cited

U.S. PATENT DOCUMENTS 6,852,503 B1 * 2/2005 Clothier .................. C12Q 1/28
252/700
9,203,080 B2 * 12/2015 Deronzier ............ C07D 279/22
2014/0221359 A1   8/2014 Wischik et al.

FOREIGN PATENT DOCUMENTS

WO       2010/0336643 A2 *  3/2010
WO       2014/080378 A1  *  5/2014
WO    WO-2018226589 A1    12/2018
WO    WO-2018226589 A9    12/2018

OTHER PUBLICATIONS

"International Application Serial No. PCT/US2018/035869, International Preliminary Report on Patentability dated Dec. 19, 2019", 6 pgs.
Jones, Corey L., et al., "Small Molecule Enhancement of 20S Proteasome Activity Targets Intrinsically Disordered Proteins", *ACS Chem Biol.*, 12(9), (2017), 2240-2247.
"", 12351241, (Feb. 7, 2007), 1-10 pgs.
"", 44561498, (Jan. 26, 2010), 1-10 pgs.
"", 101912604, (Dec. 18, 2015), 1-8 pgs.
"International Application Serial No. PCT/US2018/035869, International Search Report dated Aug. 24, 2018", 2 pgs.
"International Application Serial No. PCT/US2018/035869, Written Opinion dated Aug. 24, 2018", 4 pgs.

* cited by examiner

*Primary Examiner* — Douglas M Willis
(74) *Attorney, Agent, or Firm* — Schwegman Lundberg & Woessner, P.A.

(57) ABSTRACT

The disclosure is directed to compounds of the formula (I):

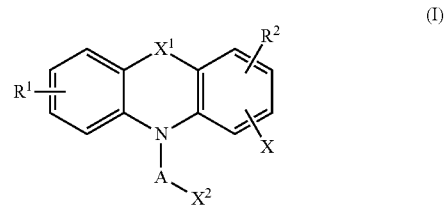

and uses of such compounds to treat neurodegenerative diseases and cancers.

9 Claims, No Drawings

SUBSTITUTED PHENOTHIAZINES AS PROTEASOME ACTIVATORS

CROSS-REFERENCE TO RELATED APPLICATIONS

This application is a U.S. national stage filing under 35 U.S.C. 371 from International Application No. PCT/US2018/035869, filed on 4 Jun. 2018, and published as WO 2018/226589 on 13 Dec. 2018, which claims benefit of priority to U.S. Provisional Appl. Ser. No. 62/515,403, filed Jun. 5, 2017, which applications are incorporated by reference as if fully set forth herein.

STATEMENT OF GOVERNMENT SUPPORT

This invention was made with government support under CA182926 awarded by the National Institutes of Health. The government has certain rights in the invention.

BACKGROUND

Proteins undergo constant proteolytic degradation to regulate intracellular processes and maintain biological homeostasis. One of the main intracellular proteolytic pathways involves the proteasome, which is responsible for the degradation of misfolded, oxidatively damaged and redundant proteins. In contrast to the 26S proteasome, which is primarily involved in ubiquitin-dependent protein degradation, intrinsically disordered proteins (IDPs), such a α-synuclein, and oxidatively damaged proteins are mainly targeted by the 20S proteasome for degradation. Disordered proteins are naturally short-lived, however basal levels are secured by forming proteolytically stable structured complexes with "nannies", chaperones or other protein complexes. However, mutations, overexpression, or proteasome dysfunction induce the process of accumulation of these non-soluble species. When accumulation of intrinsically disordered proteins exceeds proper clearance in neurons, imbalanced pathway signaling or aggregation occurs, which have been implicated in the pathogenesis of several neurological disorders, including Parkinson's disease (PD), Alzheimer's disease (AD), Huntington's disease (HD) and amyotrophic lateral sclerosis (ALS, Lou Gehrig's disease).

SUMMARY

Proteasome enhancers may offer a potential strategy to reduce the build-up of toxic proteins implicated in neurodegenerative diseases. Several studies have illustrated the enormous potential of proteasome activation as a novel treatment strategy, but very few molecules have been identified as direct or indirect enhancers of the proteasome-degradation pathway. Described herein are various are compounds that enhance 20S proteolytic activity. While not wishing to be bound by any specific theory, it is believed that the compounds described herein enhance 20S proteolytic activity via a ligand-20S proteasome interaction, which induces the selective degradation of disordered protein, α-synuclein over structured proteins in vitro. To that end, the disclosure generally relates to compounds (e.g., compounds of the formulae (I) and (II)) that are believed to act as proteasome enhancers or activators and can be used to treat disorders resulting from the accumulation of intrinsically disordered proteins that cannot be properly cleared.

DESCRIPTION

The disclosure also relates to compound of the formula (I):

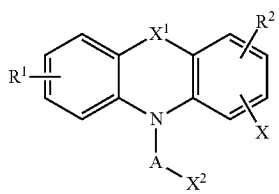

or a pharmaceutically acceptable salt, polymorph, prodrug, solvate or clathrate thereof;
wherein:
X is halo;
$X^1$ is O, S or $NR^3$, wherein $R^3$ is alkyl or arylalkyl:
$R^1$ is H, substituted or unsubstituted alkyl, substituted or unsubstituted alkoxy, substituted or unsubstituted aryl, substituted or unsubstituted aryloxy or halo;
$R^2$ is H, substituted or unsubstituted alkyl, substituted or unsubstituted alkoxy, substituted or unsubstituted aryl, substituted or unsubstituted aryloxy or halo;
A is alkylenyl, arylenyl, alkenylenyl or alkynylenyl, each of which can be substituted or unsubstituted; and
$X^2$ is H, sulfonic acid, sulfonate, carboxylic acid, ester, amide or a heterocycle.

The disclosure also relates to compound of the formula (I):

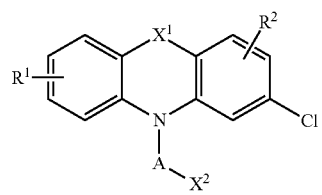

or a pharmaceutically acceptable salt, polymorph, prodrug, solvate or clathrate thereof;
wherein $X^1$ is O, S or $NR^3$, wherein $R^3$ is alkyl or arylalkyl;
$R^1$ is H, substituted or unsubstituted alkyl, substituted or unsubstituted alkoxy, substituted or unsubstituted aryl, substituted or unsubstituted aryloxy or halo;
$R^2$ is H, substituted or unsubstituted alkyl, substituted or unsubstituted alkoxy, substituted or unsubstituted aryl, substituted or unsubstituted aryloxy or halo;
A is alkylenyl, arylenyl, alkenylenyl or alkynylenyl, each of which can be substituted or unsubstituted; and
$X^2$ is H, sulfonic acid, sulfonate, carboxylic acid, ester, amide or a heterocycle (e.g., a 5- or 6-membered heterocycle optionally containing an one additional heteroatom, such as nitrogen or oxygen, in the heterocycle).

The disclosure relates to a compound of the formula (I):

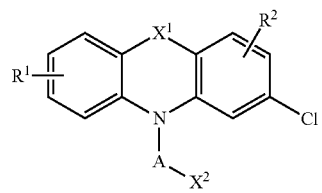

or a pharmaceutically acceptable salt, polymorph, prodrug, solvate or clathrate thereof;
wherein $X^1$ is O, S or $NR^3$, wherein $R^3$ is alkyl or arylalkyl;
$R^1$ is H, substituted or unsubstituted alkyl, substituted or unsubstituted alkoxy, substituted or unsubstituted aryl, substituted or unsubstituted aryloxy or halo;
$R^2$ is H, substituted or unsubstituted alkyl, substituted or unsubstituted alkoxy, substituted or unsubstituted aryl, substituted or unsubstituted aryloxy or halo;
A is arylenyl or alkynylenyl, each of which can be substituted or unsubstituted; and
$X^2$ is carboxylic acid or an ester.

The disclosure also relates to a compound of the formula (II):

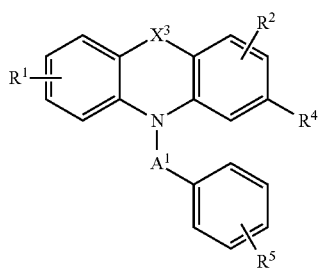

(II)

or a pharmaceutically acceptable salt, polymorph, prodrug, solvate or clathrate thereof;
wherein $X^3$ is alkylenyl, O, S or $NR^3$, wherein $R^3$ is alkyl or arylalkyl;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
$A^1$ is alkylenyl; and
$R^5$ is $C(O)OR^6$, $OR^6$, $SR^6$, $NR^6R^7$, or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) include compounds of the formula:

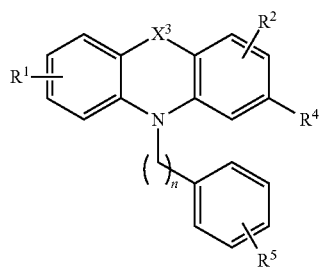

or a pharmaceutically acceptable salt, polymorph, prodrug, solvate or clathrate thereof;
wherein $X^3$ is alkylenyl or S;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
n is an integer from 1 to 5; and
$R^5$ is $C(O)OR^6$, $OR^6$, $SR^6$, $NR^6R^7$, or $C(O)NR^6R^7$ wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

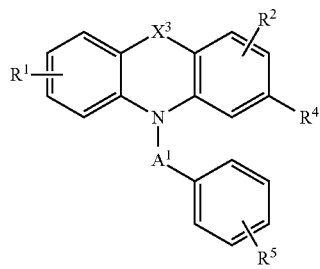

or a pharmaceutically acceptable salt, polymorph, prodrug, solvate or clathrate thereof;
wherein $X^3$ is alkylenyl or S;
$R^1$ is H;
$R^2$ is H;
$R^4$ is H, halo, trihaloalkyl, alkoxy, or alkylthio;
n is an integer from 1 to 5; and
$R^5$ is $C(O)OR^6$, $OR^6$, $SR^6$, $NR^6R^7$, or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

or a pharmaceutically acceptable salt, polymorph, prodrug, solvate or clathrate thereof;
wherein $X^3$ is alkylenyl, O, S or $NR^3$, wherein $R^3$ is alkyl or arylalkyl;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
$A^1$ is alkylenyl; and
$R^5$ is $C(O)OR^6$ or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

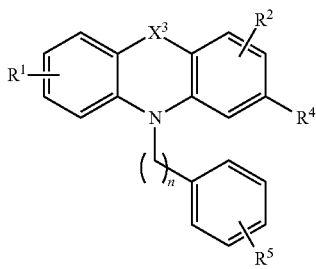

or a pharmaceutically acceptable salt, polymorph, prodrug, solvate or clathrate thereof;
wherein $X^3$ is alkylenyl or S;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
n is an integer from 1 to 5; and
$R^5$ is $C(O)OR^6$ or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

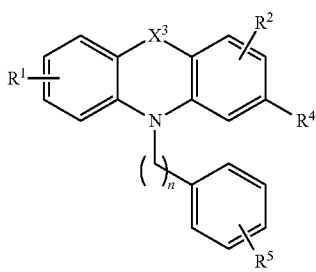

or a pharmaceutically acceptable salt, polymorph, prodrug, solvate or clathrate thereof;
wherein $X^3$ is alkylenyl or S;
$R^1$ is H;
$R^2$ is H;
$R^4$ is H, halo, trihaloalkyl, alkoxy or alkylthio;
n is an integer from 1 to 5; and
$R^5$ is $C(O)OR^6$ or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

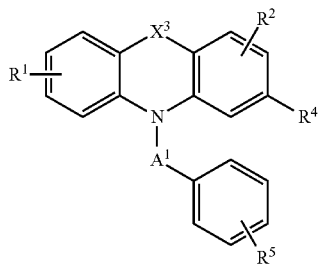

(II)

or a pharmaceutically acceptable salt, polymorph, prodrug, solvate or clathrate thereof;
wherein $X^3$ is —$(CH_2)_m$—, wherein m is an integer from 1 to 3, or S;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
$A^1$ is alkylenyl; and
$R^5$ is $C(O)OR^6$, $OR^6$, $SR^6$, $NR^6R^7$, or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) include compounds of the formula:

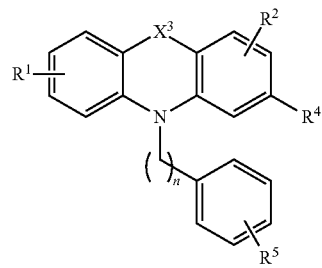

or a pharmaceutically acceptable salt, polymorph, prodrug, solvate or clathrate thereof;
wherein $X^3$ is —$(CH_2)_m$—, wherein m is an integer from 1 to 3, or S;
$R^1$ is H, alkyl, alkoxy, aryl, aryloxy or halo;
$R^2$ is H, alkyl, alkoxy, aryl, aryloxy or halo;
$R^4$ is H, halo, alkyl, alkoxy, and alkylthio;
n is an integer from 1 to 5; and
$R^5$ is $C(O)OR^6$, $OR^6$, $SR^6$, $NR^6R^7$, or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

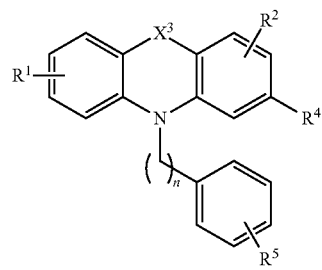

or a pharmaceutically acceptable salt, polymorph, prodrug, solvate or clathrate thereof;
wherein $X^3$ is —$(CH_2)_m$—, wherein m is an integer from 1 to 3, or S;
$R^1$ is H;
$R^2$ is H;
$R^4$ is H, halo, trihaloalkyl, alkoxy or alkylthio;
n is an integer from 1 to 5; and
$R^5$ is $C(O)OR^6$, $OR^6$, $SR^6$, $NR^6R^7$, or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

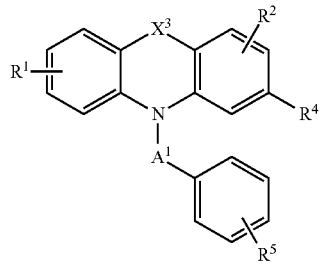

or a pharmaceutically acceptable salt, polymorph, prodrug, solvate or clathrate thereof;

wherein $X^3$ is —$(CH_2)_m$—, wherein m is an integer from 1 to 3, or S;

$R^1$ is H, alkyl, alkoxy, aryl, aryloxy or halo;

$R^2$ is H, alkyl, alkoxy, aryl, aryloxy or halo;

$R^4$ is H, halo, alkyl, alkoxy, and alkylthio;

$A^1$ is alkylenyl; and $R^5$ is $C(O)OR^6$ or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

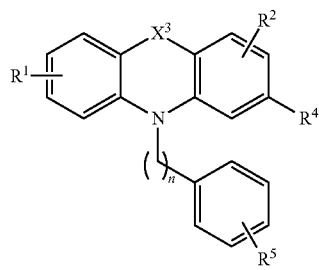

or a pharmaceutically acceptable salt, polymorph, prodrug, solvate or clathrate thereof;

wherein $X^3$ is —$(CH_2)_m$—, wherein m is an integer from 1 to 3, or S;

$R^1$ is H, alkyl, alkoxy, aryl, aryloxy or halo;

$R^2$ is H, alkyl, alkoxy, aryl, aryloxy or halo;

$R^4$ is H, halo, alkyl, alkoxy, and alkylthio;

n is an integer from 1 to 5; and $R^5$ is $C(O)OR^6$ or $C(O)NR^6R^7$, wherein $R^6$ and $R^7$ are each independently H, alkyl or aryl or $R^6$ and $R^7$, together with the nitrogen atom to which they are attached, form a heterocycle.

Compounds of the formula (II) also include compounds of the formula:

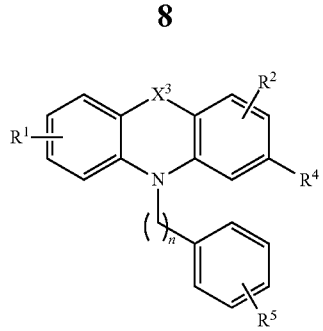

or a pharmaceutically acceptable salt, polymorph, prodrug, solvate or clathrate thereof;

wherein $X^3$ is —$(CH_2)_m$—, wherein m is an integer from 1 to 3, or S;

$R^1$ is H;

$R^2$ is H;

$R^4$ is H, halo, trihaloalkyl, alkoxy or alkylthio;

n is an integer from 1 to 5; and $R^5$ is $C(O)OR^6$ or $C(O)NR^6R^1$, wherein $R^6$ and $R^7$ are each independently H, alkyl or aryl or $R^6$ and $R^7$, together with the nitrogen atom to which they are attached, form a heterocycle.

In any of the foregoing compounds, $R^5$ can be $C(O)OR^6$ or $C(O)NR^6R^7$, wherein $R^6$ and $R^7$ are each independently H or alkyl or $R^6$ and $R^7$, together with the nitrogen atom to which they are attached, form a heterocycle. For example, $R^6$ and $R^7$ can each independently be H or a ($C_1$-$C_6$) alkyl group. Or $R^6$ and $R^7$, together with the nitrogen atom to which they are attached, can form a five- or six-membered heterocycle containing one or more additional heteroatoms in the heterocycle. For example, the heterocycle can be a six-membered heterocycle containing one additional heteroatom, where the heteroatom can be O or $NR^8$, wherein $R^8$ is H or alkyl. For example, the heterocycle can be a ring of the formula:

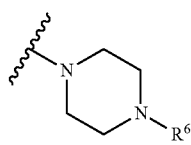

Compounds of the formula (I) include compounds of the formula:

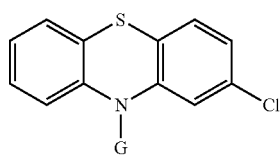

wherein G is —$(CH_2)_3CH(CH_3)_2$ (Compound (1)), —$(CH_2)_4SO_3H$ (Compound (2)), —$(CH_2)_3SO_3H$ (Compound (3)), —$(CH_2)C \equiv C \equiv CCO_2H$ (Compound (4)),

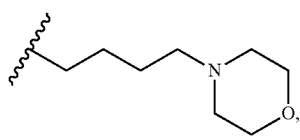
(Compound (5))
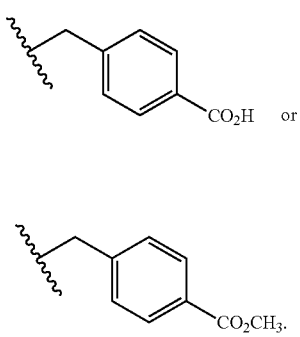
(Compound (6)) or
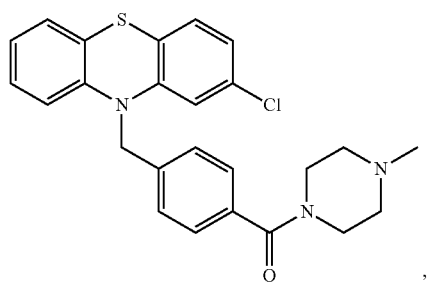
(Compound (7)).
Compounds of the formula (II) include compounds of the formulae:
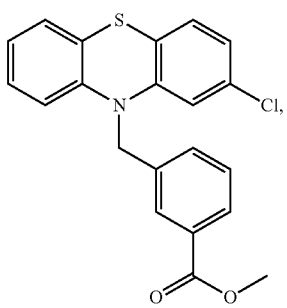
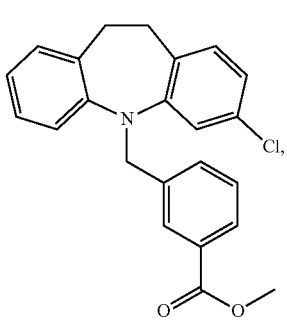
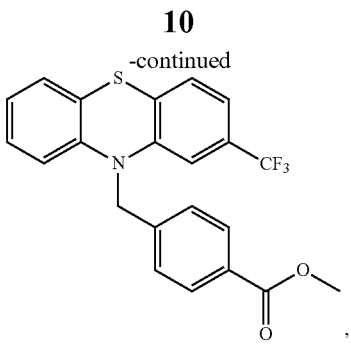
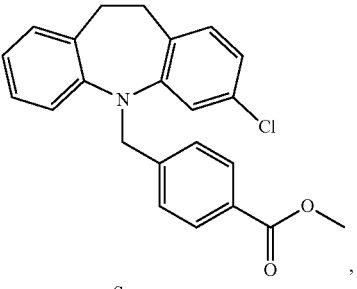
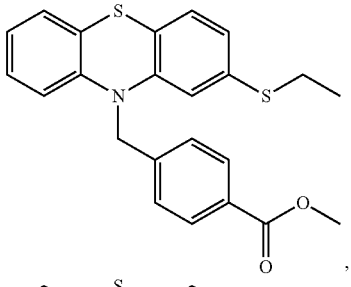
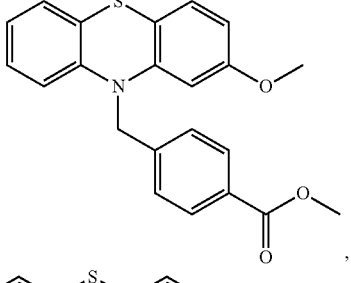
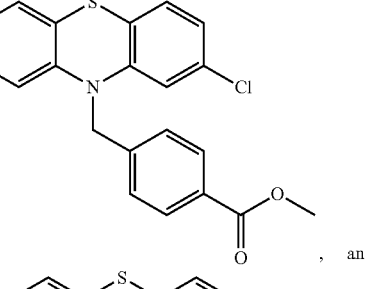
, and
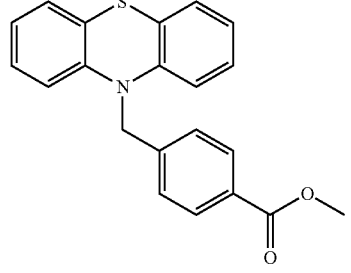
or a pharmaceutically acceptable salt, polymorph, prodrug, solvate or clathrate thereof.

The present disclosure also contemplates pharmaceutical compositions comprising one or more compounds of the formula (I) and/or (II) one or more pharmaceutically acceptable carriers, diluents, excipients or combinations thereof. A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. The carrier is suitable for, among other applications, parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

The compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphate; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition can vary according to factors such as the disease state, age, gender, weight, patient history, risk factors, predisposition to disease, administration route, pre-existing treatment regime (e.g., possible interactions with other medications), and weight of the individual. Dosage regimens can be adjusted to provide the optimum therapeutic response. For example, a single bolus can be administered, several divided doses can be administered over time, or the dose can be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and can be directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds disclosed herein or an appropriate pharmaceutical composition thereof are effective, the compounds disclosed herein can be administered in an effective amount. The dosages as suitable for this disclosure can be a composition, a pharmaceutical composition or any other compositions described herein.

The dosage can be administered once, twice, or thrice a day, although more frequent dosing intervals are possible. The dosage can be administered every day, every 2 days, every 3 days, every 4 days, every 5 days, every 6 days, and/or every 7 days (once a week). The dosage can be administered daily for up to and including 30 days, preferably between 7-10 days. Or the dosage can be administered twice a day for 10 days. If the patient requires treatment for a chronic disease or condition, the dosage can be administered for as long as signs and/or symptoms persist. The patient may require "maintenance treatment" where the patient is receiving dosages every day for months, years, or the remainder of their lives. In addition, the composition can effect prophylaxis of recurring symptoms. For example, the dosage can be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Also contemplated herein are compositions comprising a therapeutically effective amount of one or more compounds that are useful in a method for reducing the accumulation of intrinsically disordered proteins (IDPs), including α-synuclein, tau, SOD1, polyQ, oxidatively damaged proteins, c-Fos, c-Myc, and the BCL-2 family of disordered proteins, in a subject, the method comprising administering a therapeutically effective amount of one or more compounds of the formula (I) and/or (II) to a patient in need thereof. Also contemplated herein is a compound of the formula (I) and/or (II) for use as a medicament for treating a patient in need of relief from the accumulation of intrinsically disordered proteins (IDPs), including α-synuclein, tau, SOD1, polyQ, oxidatively damaged proteins, c-Fos, c-Myc, and the BCL-2 family of disordered proteins.

Also contemplated herein are compositions comprising a therapeutically effective amount of one or more compounds that are useful in a method for treating various conditions associated with the accumulation of IDPs, including neurological disorders (e.g., Parkinson's disease (PD), Alzheimer's disease (AD), Huntington's disease (HD) and amyotrophic lateral sclerosis (ALS, Lou Gehrig's disease)); and cancers associated with the accumulation of IDPs such as c-Fos, c-Myc, and the BCL-2 family of disordered proteins (e.g., myeloid leukemia, glioblastoma, melanoma, breast cancer, colon cancer, cervical cancer, small-ceil lung carcinoma, and osteosarcoma). Also contemplated herein is a compound of the formula (I) and/or (II) for use as a medicament for treating a patient in need of relief from neurological disorders or cancers associated with the accumulation of IDPs such as c-Fos, c-Myc, and the BCL-2 family of disordered proteins.

The term "neurological disorders" and "neurodegenerative diseases" are used herein interchangeably.

The term "therapeutically effective amount" as used herein, refers to that amount of one or more compounds of the formula (I) and/or (II) that elicits a biological or medicinal response in a tissue system, animal or human, that is being sought by a researcher, veterinarian, medical doctor or other clinician, which includes alleviation of the symptoms of the disease or disorder being treated. The therapeutically effective amount can be that which may treat or alleviate the disease or symptoms of the disease at a reasonable benefit/risk ratio applicable to any medical treatment. However, it is to be understood that the total daily usage of the compounds and compositions described herein can be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

The present disclosure also contemplates compounds of the formula (I) and/or (II) having a 20S proteasome chymotryptic-like (CT-L) activity $EC_{50}$ value of less than 250 µM, less than 150 µM, less than 100 µM, less than 50 µM, less than 25 µM, less than 10 µM, less than 1 µM, less than 500 nM; or from about 1 nM to about 1 µM, about 1 µM to about 50 µM, about 1 µM to about 20 µM, about 1 nM to about 200 nM, about 50 nM to about 500 nM or about 10 nM to about 150 nM.

The present disclosure also contemplates compounds of the formula (I) and/or (II) having a % inhibition of [3H]-spiperone binding at the D2R of at least about 10%, at least about 20%, at least about 30%, at least about 40%, at least about 50%, at least about 60%, at least about 70%, at least about 80%, at least about 90%, at least about 99%; or about 20% to about 100%, about 30% to about 90%, about 40% to about 95%, about 50% to about 90% or about 70% to about 95%.

The present disclosure also contemplates compounds of the formula (I) and/or (II) having a Ki of chlorpromazine (CPZ) of less than 250 µM, less than 150 µM, less than 100 µM, less than 50 µM, less than 25 µM, less than 10 µM, less than 1 µM, less than 500 nM; or from about 1 nM to about 1 µM, about 1 µM to about 50 µM, about 1 µM to about 20 µM, about 1 nM to about 200 nM, about 50 nM to about 500 nM or about 10 nM to about 150 nM.

The present disclosure also contemplates compounds of the formula (I) and/or (II) having a combination of at least two of the aforementioned $EC_{50}$ values, % inhibition, and Ki values; and in some cases all three of aforementioned $EC_{50}$ values, % inhibition, and Ki values for a single compound.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the spirit of this disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$ (an example of an amide), OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), from 1 to 6 carbon atoms ($C_1$-$C_6$) or 1 to 3 ($C_1$-$C_3$) carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed herein, for example, amino, hydroxy, cyano, carboxy, nitro, thio, alkoxy, and halogen groups.

As used herein, the term "alkylenyl" broadly refers to substituted or unsubstituted divalent straight chain and branched alkylenyl groups having from 1 to 40 carbon atoms ($C_1$-$C_{40}$), from 1 to about 20 carbon atoms ($C_1$-$C_{20}$), from 1 to 12 carbons ($C_1$-$C_{12}$), from 1 to 8 carbon atoms ($C_1$-$C_8$), or, in some examples, from 1 to 6 carbon atoms ($C_1$-$C_6$). Examples of straight chain divalent alkylenyl groups include those with from 1 to 8 carbon atoms such as ethyl (—CH$_2$CH$_2$—), n-propyl (—CH$_2$CH$_2$CH$_2$—), n-butyl (—CH$_2$CH$_2$CH$_2$CH$_2$—), n-pentyl (—CH$_2$CH$_2$CH$_2$CH$_2$CH$_2$—), n-hexyl (—CH$_2$CH$_2$CH$_2$CH$_2$CH$_2$CH$_2$—), n-heptyl (—CH$_2$CH$_2$CH$_2$CH$_2$CH$_2$CH$_2$CH$_2$—), and n-octyl (—CH$_2$CH$_2$CH$_2$CH$_2$CH$_2$CH$_2$CH$_2$CH$_2$—) groups.

As used herein, the term "alkenylenyl" broadly refers to substituted or unsubstituted divalent straight chain and branched alkenylenyl groups having from 1 to 40 carbon atoms ($C_1$-$C_{40}$), from 1 to about 20 carbon atoms ($C_1$-$C_{20}$), from 1 to 12 carbons ($C_1$-$C_{12}$), from 1 to 8 carbon atoms ($C_1$-$C_8$), or, in some examples, from 1 to 6 carbon atoms ($C_1$-$C_6$). Examples of straight chain divalent alkenylenyl groups include those with from 1 to 8 carbon atoms such as ethylenyl (—CH═CH—), n-propenyl (—CH═CHCH$_2$—), n-butenyl (—CH═CHCH$_2$CH$_2$—), and the like.

As used herein, the term "alkynylenyl" broadly refers to substituted or unsubstituted divalent straight chain and branched alkynylenyl groups having from 1 to 40 carbon atoms ($C_1$-$C_{40}$), from 1 to about 20 carbon atoms ($C_1$-$C_{20}$), from 1 to 12 carbons ($C_1$-$C_{12}$), from 1 to 8 carbon atoms ($C_1$-$C_8$), or, in some examples, from 1 to 6 carbon atoms ($C_1$-$C_6$). Examples of straight chain divalent alkynylenyl groups include those with from 1 to 8 carbon atoms such as ethynyl (—C≡C—CH$_2$—), n-propynyl (—C≡C—CH$_2$—), and the like.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. The cycloalkyl group can have 3 to about 8-12 ring members, whereas the number of ring carbon atoms can range from 3 to 4, 5, 6, or 7. Cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "arylenyl" as used herein refers to divalent groups that are derived by removing two hydrogen atoms from an "arylalkyl" group. Examples of arylenenyl groups include the group:

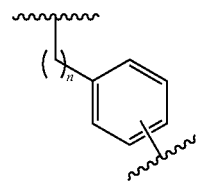

wherein the wavy lines represent the points of attachment.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. Heterocyclyl groups can include 3 to about 20 ring members, whereas other such groups have 3 to about 15 ring members. Heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an example of a heterocyclyl group. The phrase "heterocyclyl group" includes fused ring species including those that include fused aromatic and non-aromatic groups. Representative heterocyclyl groups include, but are not limited to piperidinyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to alkylamines, arylamines, arylalkylamines;

dialkylamines, diarylamines, diaralkylamines, heterocyclylamines and the like; and ammonium ions.

The terms "halo," "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound according to the instant disclosure. Examples of prodrugs include, but are not limited to, derivatives and metabolites of compounds described herein that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The following examples are offered by way of illustration. But the present disclosure is not limited to the examples given herein.

Materials and Methods

Human proteasomes (20S, 26S) and fluorogenic substrates; N-Succinyl-Leu-Leu-Val-Tyr-7-amido-4-methylcoumarin (Suc-LLVY-AMC), carboxyl benzyl-Leu-Leu-Glu-7-amido-4-methylcoumarin (Z-LLE-AMC), tert-(Boc-LRR-AMC), acetyl-Pro-Ala-Leu-7-amido-4-methylcoumarin (Ac-PAL-AMC), and bortezomib were obtained from Boston Biochem (Cambridge, Mass.). Nitrocellulose membrane, Clarity western ECL reagent, blocking grade milk, and precast SDS gels were from Bio Rad (Hercules, Calif.). Recombinant wild type α-synuclein and GAPDH were bought from Abram (Cambridge, Mass.). Rabbit polyclonal anti-α-synuclein (C-20), goat anti-rabbit-HRP, and rabbit polyclonal GAPDH-HRP were purchased from Santa Cruz Biotechnologies. Compounds used for HTS were obtained from the NIH Clinical Collection and Prestwick libraries, through the MSU Assay Development and Drug Repurposing Core (ADDRC). Fresh phenothiazines (Table 1) were obtained from Sigma Aldrich (St. Louis, Mo.).

Proteasome activity assay: Activity assays were carried out in a 200 µL reaction volume. Different concentrations of test compounds were added to a black flat/clear bottom 96-well plate containing 1 nM of either human constitutive 20S proteasome, or 26S proteasome, in 50 mM Tris-HCl pH 7.5 and allowed to sit for 10 minutes at RT. Fluorogenic substrates were then added and the enzymatic activity measured at 37° C. on a SpectraMax M5e spectrometer by measuring increase in fluorescence unit per minute for 1 hour at 380-460 nm. The fluorescence units for the vehicle control was set at a 100% and the ratio of drug-treated sample to that of vehicle control was used to calculate fold change in enzymatic activity. Fold activity was plotted as a function of drug concentration, using graphpad prism 5. The fluorogenic substrates used were Suc-LLVY-AMC (CT-L activity, 10 µM), Z-LLE-AMC (Casp-L activity, 10 µM). Boc-LRR-AMC (Tryp-L activity, 20 µM). Magnesium chloride (5 mM) and ATP (2.5 mM) were included in assays containing 26S proteasome. Using 384 well plates, HTS was carried out in 384-well plates as described above with the exceptions that each compound was tested at a single concentration (10 µM), and dispensing of assay reagents and compounds was automated.

Docking Studies. The crystal structure of the closed gate human proteasome was obtained from the PDB database (PDB ID: 4R3O). Molecules were generated in ChemBio3D, minimized using the MM2 force field, and converted to PDB. Docking was conducted in three stages utilizing AutoDock Vina™ mated to Pyrx™. Stage I. Each identified hit compound was docked against the entirety of the h20S proteasome (grid box 153.2×138.0×189.4 Å) 3 times per compound with exhaustiveness set to 60. Active compounds displayed a preference for the α-rings. Stage II Following results from Stage I, docking was resubmitted with new center at (136.2, −40.6, 60.5) and grid box dimensions reduced to 125.0×138.0×71.6 Å and exhaustiveness left at 60 (Fig. S5A). Stage II revealed numerous bound poses of each compound within the α-ring intersubunit pocket.

Stage III The binding pocket was isolated with a center at (159.7, −63.9, 69.8) and dimensions 30.98×28.6×30.1 Å. Exhaustiveness was raised to 80. Individual poses were manually inspected with higher energy binding poses preferred. Potential compounds to synthesize were docked in the same manner and those with similar binding preferences were synthesized and checked for 20S mediated CT-L activity.

D2R binding assay: Human Embryonic Kidney (HEK-293) cells were plated in 100-mm plates and transfected with pcDNA3.1-D2R using Lipofectamine 2000 (Invitrogen; Waltham, Mass.) according to the manufacturer's instructions. Radioligand binding assays were performed 24 h after transfection essentially as described. Cells were harvested in PBS and centrifuged for 5 min at 2000×g. Cells were re-suspended in Optimem media (Invitrogen) to 106 cells/ml. 50 µl Cell suspension (50,000 cells/well), 50 µl 1.5 nM [3H]-Spiperone (D2R antagonist) and 50 µl vehicle or displacing agents were added to wells in a 96-well microtiter plate. Binding reactions were allowed to reach equilibrium for 90 min at room temperature. Assays were terminated by rapid filtration over glass fiber filters using a Brandel cell harvester (Brandel; Gaithersburg, Md.). Filters were thereafter washed with 5 mL ice-cold PBS before being transferred to scintillation vials and incubated with 3 mL scintillation fluid (Ultima Gold; Perkin Elmer; Akron Ohio), at room temperature overnight. Vials were counted in a β-counter (Wallac 1209 Rackbeta; Perkin Elmer) for 2 min/vial. All experiments were performed with duplicate samples. Data was analyzed with non-linear regression using GraphPad Prism.

In vitro degradation of α-synuclein: Digestion of α-synuclein was carried out in a 50 µL reaction volume made of 20 mM HEPES pH 7.4, 2 mM EDTA, 1 mM EGTA, 0.5 µM purified α-synuclein, 0.5 µM GAPDH, and 15 nM purified human 20S proteasome. Briefly, 20S proteasome was diluted to 17 nM in the reaction buffer. Test compounds or vehicle (1 µL of 50× stock) were added to 44 µL of 17 nM 20S and incubated at RT for 20 minutes. The substrate (5 µL of 5 µM GAPDH/synuclein mixture) was then added to the reaction mixture and incubated at 37° C. for 1 hour. The reactions were quenched with concentrated SDS-loading buffer. After boiling for 5 minutes, samples were resolved on a 4-20% Tris-glycine SDS-PAGE and immunoblotted with rabbit polyclonal anti α-synuclein IgG (1:4000) and goat anti-rabbit HRP (1:5000)/anti-GAPDH-HRP. Blots were developed with ECL western reagent and imaged with x-ray film.

Statistical analyses: Data are presented as mean±standard deviation of at least three independent experiments. Western blots were quantified with imageJ and statistical analysis done with GraphPad Prism 5 software. Unpaired Student's t-test was used for two samples while one-way analysis of variance with post hoc Bonferroni test was used for multiple comparisons of means Examples 1-9: Synthesis of Compounds (1)-(9)

The compounds of the various embodiments can be synthesized as described in the following examples. The compounds of the formulae (I) and (1)-(7) can be synthesized according to the methods presented herein and presented in Scheme I. The compounds of the formula (II) can be synthesized using analogous methods.

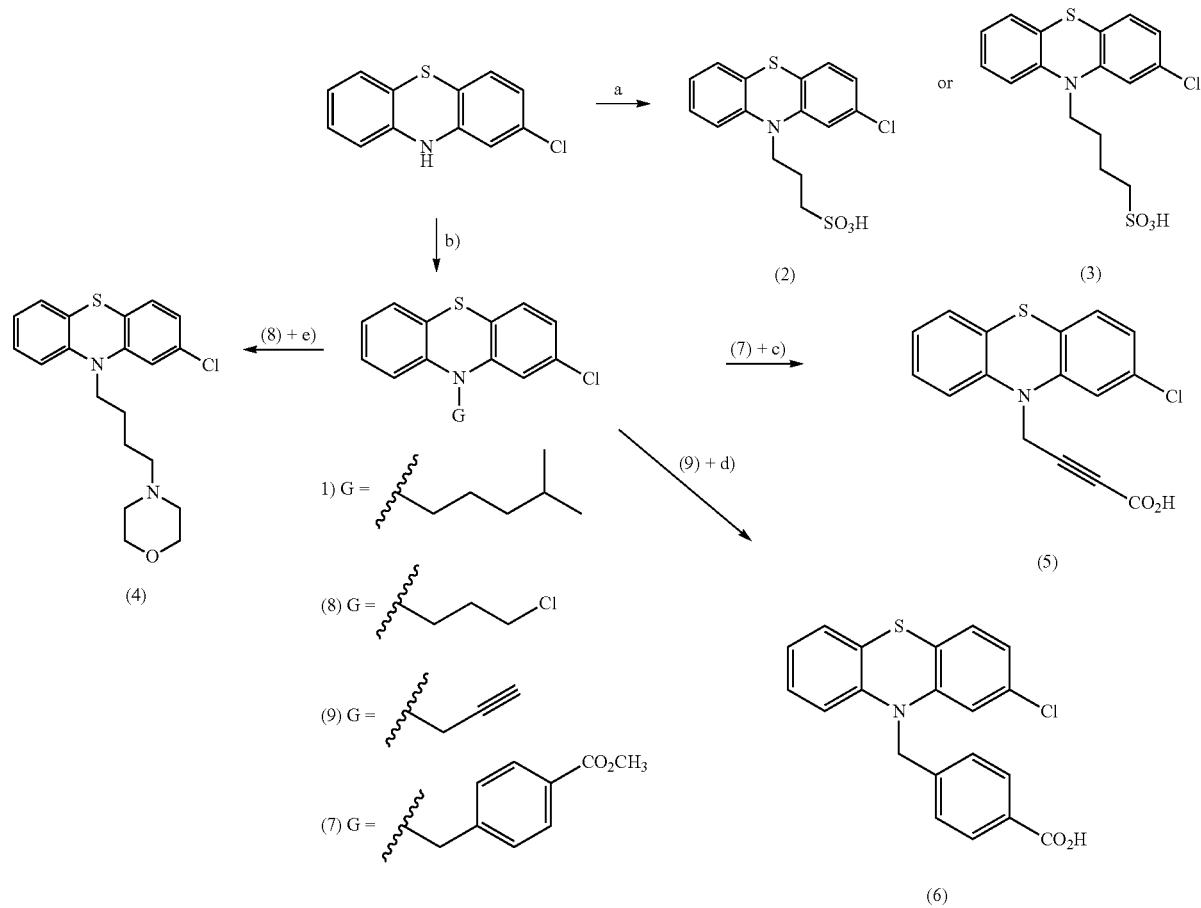

a) NaH, THF, reflux 1 hr, then addition of sulfone reflux 12 hours, cool to room temperature; b) NaH, THF, reflux 1 hour then add alkyl halide; c) i) NaI, acetone, reflux 48 hours, ii) morpholine neat, reflux 2 hours; d) nBuLi, THF, -78° C., 20 minutes, then CO₂ 2 hours, warm to 10° C.; e) KOH, EtOH/Water (1:1), reflux 12-16 hours.

2-Chloro-10-(4-methylpentyl)-10H-phenothiazine (1) A solution of 2-chloro-10H-phenothiazine (0.467 g, 2 mmol) in THF is added dropwise to a suspension of sodium hydride (60% wt/wt, 0.080 g, 2 mmol) at room temperature. The mixture is allowed to stir at room temp for 30 minutes. 1-Bromo-4-methyl pentane (0.146 mL, 1 mmol) was added neat, dropwise. After stirring for 2 hours, the solution was poured into saturated bicarbonate solution (ca. 50 mL) and extracted into ethyl acetate (3×50 mL). The combined organic layers were washed with brine (ca. 50 mL) and dried over sodium sulfate and concentrated in vacuo to give a purple solid. The solid was slurried in dichloromethane and applied to an auto column to give the final product as a white solid (85.1 mg, 26.8%). $^{13}$C NMR (126 MHz, CDCl$_3$) δ 146.7, 144.7, 133.3, 128.0, 127.6, 127.5, 124.8, 123.5, 122.9, 122.2, 115.8, 115.8, 47.9, 36.2, 27.8, 24.8, 22.7. $^1$H NMR (500 MHz, CDCl$_3$) δ 7.20-7.10 (m, 2H), 7.02 (d, J=8.2 Hz, 1H), 6.93 (td, J=7.5, 1.1 Hz, 1H), 6.88 (dd, J=8.1, 2.0 Hz, 1H), 6.85 (dd, J=8.2, 1.1 Hz, 1H), 6.81 (d, J=2.0 Hz, 1H), 3.78 (t, J=7.2 Hz, 2H), 1.82-173 (m, 2H), 1.59-1.51 (m, 1H), 1.34-1.24 (m, 2H), 0.88 (d, J=6.6 Hz, 6H). HRMS (ESI) m/z. [M+H]$^+$ Calc'd for C$_{18}$H$_{22}$ClNS: 318.1083; Found 318.1082. ATIR: aromatic CH (3176 cm$^-$ and 3056 cm$^{-1}$), CH (2952 cm$^{-1}$).

4-(2-Chloro-10H-phenothiazin-10-yl) butane-1-sulfonate (2) 2-Chloro-10H-phenothiazine (3.5 g, 15 mmol) was added as a solution in anhydrous THF (10 mL) to a round bottomed flash charged with sodium hydride (0.6 g, 15 mmol) and THF (15 mL). The solution was then heated to reflux for 1 hour to give a bright red solution which was cooled to near room temperature and injected with 1,4-butane sultone (1.54 mL, 15 mmol). The solution was then refluxed for 24 hours. Upon cooling, title compound precipitated from solution as an off white solid (4.6 g, 78%) and can be used without further purification. Further purification can be achieved if desired by taking a portion of the compound and refluxing with benzene overnight (ca. 12 h) with a dean-stark trap. Benzene solution was then frozen and sublimed off to give clean compound. $^{13}$C NMR (126 MHz, DMSO-d$_6$): δ 146.4, 144.0, 132.5, 128.1, 127.8, 127.2, 123.2, 122.9, 122.5, 122.0, 116.3, 115.7, 50.9, 46.5, 25.5, 22.6. $^1$H NMR (500 MHz, DMSO-d$_6$): δ 7.19 (t, J=7.7 Hz, 1H), 7.15-7.10 (m, 2H), 7.06-7.01 (m, 2H), 6.99-6.93 (m, 2H), 3.84 (t, J=6.7 Hz, 2H), 2.42 (t, J=7.4 Hz, 2H), 1.74-1.62 (m, 4H). HAMS (ESI) m/z: [M+H]$^+$ Calc'd for C$_{16}$H$_{17}$ClNO$_3$S 370.0338; Found 370.0344. ATIR: Aromatic CH (3427 cm$^{-1}$), CH (2950 cm$^{-1}$, very weak) RSO$_3$— (1049 cm$^{-1}$).

3-(2-Chloro-10H-phenothiazin-10-yl) propane-1-sulfonate (3) 2-Chloro-10H-phenothiazine (0.981 g, 4.2 mmol) was added as a solution in anhydrous THF (10 mL), to a round bottomed flash charged with sodium hydride (0.160 g, 4 mmol) and THF (15 mL). The solution was then heated to reflux for 1 hour to give a bright red solution which was cooled to near room temperature before addition of 1,3-propane sultone (0.41 mL, 4 mmol). The solution immediately becomes yellow and forms a white precipitate. The solution was stirred for 1 hr at reflux and the precipitate collected upon cooling. The white solids form upon cooling and were washed with THF (100 mL) and diethyl ether (100 mL) before being left to dry in air overnight (985 mg, 65%). $^{13}$C NMR (126 MHz, DMSO-d$_6$) δ 146.3, 144.0, 132.5, 128.1, 127.8, 127.2, 123.1, 122.9, 122.4, 122.1, 116.3, 115.7, 48.5, 45.7, 22.7. $^1$H NMR (500 MHz, DMSO-d$_6$) δ 7.21 (ddd, J=8.6, 7.3, 1.6 Hz, 1H), 7.16-7.12 (m, 2H), 7.07 (dd, J=8.3, 1.5 Hz, 2H), 7.01-6.93 (m, 2H), 3.99 (t, J=7.2 Hz, 2H), 2.53 (t, J=7.3 Hz, 2H), 1.96 (tt, J=8.4, 6.5 Hz, 2H). HRMS (ESI) m/z [M+H]$^+$ Calc'd for C$_{15}$H$_{15}$ClNO$_3$S$_2$ 356.0182; Found 356.0182 ATIR: Aromatic CH (3427 cm$^{-1}$), CH (2950 cm$^{-1}$, very weak) RSO$_3^-$ (1049 cm$^{-1}$).

4-(4-(2-Chloro-10H-phenothiazin-10-yl) butyl) morpholine (4) 2-Chloro-10-(4-iodobutyl)-10H-phenothiazine was added to a neat solution of morpholine and gently refluxed for 2 hours. The solution was poured into separatory funnel containing 0.5M HCl solution. The aqueous layer was extracted with EtOAc (2×100 mL), and the combined organic layers washed with brine (100 mL), dried over sodium sulfite and concentrated in vacuo to give the title compound in quantitative yield. $^{13}$C NMR (126 MHz, CDCl$_3$) δ 146.6, 144.7, 133.3, 128.0, 127.7, 127.5, 124.9, 123.7, 123.0, 122.6, 115.9, 115.9, 67.1, 58.3, 53.8, 47.3, 24.4, 23.6. $^1$H NMR (500 MHz, CDCl$_3$) δ 7.15 (ddd, J=8.1, 7.4, 1.6 Hz, 1H), 7.12 (dd, J=7.7, 1.5 Hz, 1H), 7.02 (d, J=8.1 Hz, 1H), 6.93 (td, J=7.5, 1.2 Hz, 1H), 6.88 (dt, J=8.2, 1.8 Hz, 2H), 6.83 (d, J=2.0 Hz, 1H), 3.86 (t, J=6.9 Hz, 2H), 3.66 (t, J=4.6 Hz, 4H), 2.36 (dd, J=14.9, 7.7 Hz, 6H), 1.85 (tt, J=7.7, 6.2 Hz, 2H), 1.62 (p, J=7.3 Hz, 2H), HRMS (ESI) m/z: [M+H]$^+$ Calc'd for C$_{20}$H$_{24}$ClN$_2$OS 375.1298; found: 375.1306. ATIR: Aromatic CH (3100 cm$^{-1}$), CH (2945 cm$^{-1}$), CH (2846 cm$^{-1}$).

4-(2-Chloro-10H-phenothiazin-10-yl) but-2-ynoic acid (5) A solution of 2-chloro-10-(prop-2-yn-1-yl)-10H— phenothiazine (0.338 g, 1.25 mmol) in THF was cooled to −78° C. in an acetone/dry ice bath and allowed to stand one n hexanes, 0.52 mL, 1.31 mmol) was added dropwise and allowed to stir for ca. 20 min. An excess of solid carbon dioxide was added and the round bottom flask sealed. The reaction was allowed to stir for 2 hours before warming to 10° C. Solution was then poured into a small beaker containing 10% HCl solution (pH ~2) and extracted into ether. The organic layer was adjusted with 10% NaOH to a pH of 11, organic layer discarded, and the aqueous layer acidified to 2 by the addition of 10% HCl. The aqueous layer was then extracted into ether, washed with brine, dried using sodium sulfate, and concentrated in vacuo to give the product as a light brown solid (0.078 g, 20%). $^{13}$C NMR (126 MHz CDCl$_3$) δ 156.0, 144.9, 143.1, 133.6, 127.9, 127.8, 127.4, 123.9, 123.3, 123.3, 122.2, 115.0, 115.0, 83.9, 77.8, 38.7. $^1$H NMR (500 MHz, CDCl$_3$) δ 7.16 (d, J=7.8 Hz, 1H), 7.09 (d, J=7.6 Hz, 1H), 7.05 (d, J=8.1 Hz, 1H), 7.00 (d, J=7.9 Hz, 2H), 6.95 (t, J=7.6 Hz, 1H), 6.91 (dd, J=8.1, 1.9 Hz, 1H), 4.60 (s, 2H). HRMS (ESI) m/z: [M+H]$^+$ Calc'd for C$_{16}$H$_{11}$ClNO$_2$S 316.0189; Found 316.0201, ATIR CO$_2$H (br, 3400 cm$^{-1}$-2700 cm$^{-1}$), —C≡C—CO$_2$ (2236 cm$^{-1}$)

4-((2-Chloro-10H-phenothiazin-10-yl) methyl) benzoic acid (6) Methyl 4-((2-chloro-10H-phenothiazin-10-yl) methyl)benzoate (0.400 g, 1.05 mmol) was added to a solution of 10% NaOH and methanol (1:1) and refluxed for 2 hours. The reaction was extracted with ether and the organic layer discarded. The aqueous layer was acidified with 10% HCl to pH 2 and extracted into ether (50 washed with brine (50 mL), dried over sodium sulfate. The resulting solution was concentrated in vacuo to give a white solid (0.376 g, 97%). $^{13}$C NMR (126 MHz, CDCl$_3$) δ 171.1, 145.7, 143.7, 142.7, 133.3, 131.0, 128.5, 127.7, 127.6, 127.3, 126.9, 123.5, 123.4, 122.8, 122.3, 115.8, 115.7, 52.6. $^1$H NMR (500 MHz, CDCl$_3$) δ 8.09 (d, J=8.2 Hz, 2H), 7.43 (d, J=8.1 Hz, 2H), 7.10 (dd, J=7.6, 1.5 Hz, 1H), 7.06-6.95 (m, 2H), 6.93-6.81 (m, 2H), 6.62-6.50 (m, 2H), 5.12 (s, 2H). HAMS (ESI) m/z. [M−H]$^-$ Calc'd for C$_{20}$H$_{13}$ClNO$_2$S 366.0356; Found 366.0356 ATIR OH (w, br, 3433 cm$^{-1}$), CH Aromatic (2995 cm$^{-1}$), CH (2912 cm$^{-1}$), CO (w, 1610 cm$^{-1}$).

Methyl 4-((2-chloro-10H-phenothiazin-10-yl)methyl) benzoate (7) 2-Chloro-10H-phenothiazine (0.583 g, 2.5 mmol) was added as a solution in anhydrous THF (ca. 15), to a round bottomed flash charged with sodium hydride (0.090 g, 2.25 mmol). The mixture was stirred at room temperature for 1 hour followed by addition of 4-bromomethyl benzoate (0.458 g, 2 mmol). Upon addition, the reaction becomes a brown-orange solution and was covered in foil before stirring for 4 days, after which the solution was green. The solution was poured into a seperatory funnel containing diethyl ether and turned purple. Saturated sodium bicarbonate was added and the aqueous layer (brown in color) was discarded. The organic layer was washed with brine, dried over sodium sulfate and concentrated in vacuo to give the crude product. The crude was suspended in chloroform and placed in a −20° C. freezer overnight to precipitate out unreacted starting material. The solution was decanted and the chloroform concentrated in vacuo to give the pure product as a white solid (0.700 g, 92%). $^{13}$C NMR (126 MHz, CDCl$_3$) δ 166.9, 145.7, 143.7, 141.6, 133.3, 130.3, 130.3, 129.5, 127.6, 127.6, 127.2, 126.8, 123.3, 122.7, 115.8, 115.7, 52.6, 52.3. $^1$H NMR (500 MHz, CDCl$_3$) δ 8.01 (d, J=8.3 Hz, 2H), 7.42-7.35 (m, 2H), 7.09 (dd, J=7.6, 1.6 Hz, 1H), 7.00 (d, J=8.2 Hz, 1H), 6.89 (td, J=7.5, 1.2 Hz, 1H), 6.85 (dd, J=8.2, 2.0 Hz, 1H), 6.60-6.54 (m, 3H), 5.09 (s, 2H), 3.91 (s, 3H). HRMS (ESI) m/z: [M+H]$^+$ Calc'd for C$_{21}$H$_{17}$ClNO$_2$S 382.0669; Found 382.0670. ATIR Aromatic CH (3100 cm$^{-1}$), CH (2949 cm$^{-1}$, 2922 cm$^{-1}$), CO (st, sharp, 1716 cm$^{-1}$).

2-Chloro-10-(4-iodobutyl)-10H-phenothiazine (8) 2-Chloro-10-(4-chlorobutyl)-10H-phenothiazine (6.00 g, 18.5 mmol) was dissolved in acetone (150 mL). Finely ground sodium iodide (ca. 50 g, 333 mmol) was added and the mixture vigorously stirred. The mixture was refluxed for 3 days. The mixture was then placed in a −20° C. freezer for 4 hours and then filtered through a medium frit. Solids were washed with acetone (2×100 mL) and the filtrate concentrated to dryness to give the product as a waxy brown solid in quantitative yield (7.6 g). $^{13}$C NMR (126 MHz, CDCl$_3$) δ 146.0, 14.3.9, 132.9, 127.8, 127.4, 127.2, 124.7, 123.5, 122.8, 122.1, 115.6, 115.5, 45.9, 30.3, 27.2, 6.6. $^1$H NMR (500 MHz, CDCl$_3$) δ 7.20 (ddd, J=15.8, 7.7, 1.5 Hz, 2H), 7.03 (d, J=8.2 Hz, 1H), 6.98 (td, J=7.5, 1.1 Hz, 1H), 6.91 (dd, J=8.1, 2.0 Hz, 1H), 6.87-6.82 (m, 2H), 3.79 (t, J=6.2 Hz, 2H), 3.14 (t, J=6.3 Hz, 2H), 1.97-1.84 (m, 4H). HRMS (ESI) m/z: Calc'd for C$_{16}$H$_{16}$ClINS 415.9737; Found 415.9745. ATIR Aromatic CH (3150 cm−1), CH (2921 cm$^{-1}$, 2852 cm$^{-1}$).

2-Chloro-10-(prop-2-yn-1-yl)-10H-phenothiazine (9) 2-Chloro-10H-phenothiazine (0.467 g, 2 mmol) was added as a solution in anhydrous THF (ca. 10 mL), to a round bottomed flash charged with sodium hydride (0.076 g, 1.9 mmol). The solution was stirred one hour to give a reddish-brown solution before the addition of propargyl bromide (80% in Toluene, 0.24 mL, 2.2 mmol) in a single portion. The solution was stirred for 12 hours and then concentrated to dryness in vacuo before being placed on a high vacuum line for approximately 4 hours. Crude material was suspended in chloroform and cooled to −20° C. overnight. The starting material precipitates out and was removed by filtration. The filtrate was concentrated to dryness to give thick, dark oil as product (0.300 g, 58.1%) which was used in the next step without further purification. $^{13}$C NMR (126 MHz CDCl$_3$) δ 145.4, 143.7, 133.5, 127.8, 127.6, 127.2, 123.5, 123.3, 122.9, 122.1, 115.3, 115.2, 78.6, 75.1, 38.8. $^1$H NMR (500 MHz, CDCl$_3$) δ 7.23-7.18 (m, 3H), 7.13 (dd, J=7.6, 1.4 Hz, 1H), 7.02 (d, J=8.2 Hz, 1H), 6.98 (ddd, J=7.8, 6.7, 2.0 Hz, 1H), 6.93 (dd, J=8.2, 2.0 Hz, 1H), 4.48 (d, J=2.4 Hz, 2H), 2.51 (t, J=2.4 Hz, 1H), HRMS (ESI) m/z: [MI $^-$Calc'd for C15H10ClNS 271.0222; Found 271.0228.

The disclosure provides for the following embodiments, the numbering of which is not to be construed as designating levels of importance:

Embodiment 1 relates to a compound of the formula (I):

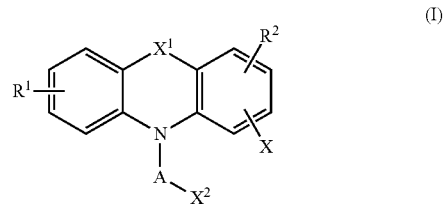

or a pharmaceutically acceptable salt, polymorph, prodrug, solvate or clathrate thereof; wherein:

X is halo;

X$^1$ is O, S or NR$^3$, wherein R$^3$ is alkyl or arylalkyl;

R$^1$ is H, substituted or unsubstituted alkyl, substituted or unsubstituted alkoxy, substituted or unsubstituted aryl, substituted or unsubstituted aryloxy or halo;

R$^2$ is H, substituted or unsubstituted alkyl, substituted or unsubstituted alkoxy, substituted or unsubstituted aryl, substituted or unsubstituted aryloxy or halo;

A is alkylenyl, arylenyl, alkenylenyl or alkynylenyl, each of which can be substituted or unsubstituted; and X$^2$ is H, sulfonic acid, sulfonate, carboxylic acid, ester, amide or a heterocycle.

Embodiment 2 relates to the compound of Embodiment 1, wherein X is halo.

Embodiment 3 relates to the compound of Embodiments 1-2, wherein X is chloro.

Embodiment 4 relates to the compound of Embodiments 1-3, wherein X$^1$ is S.

Embodiment 5 relates to the compound of Embodiments 1-4, wherein R$^1$ and R$^2$ are each H.

Embodiment 6 relates to the compound of Embodiments 1-5, wherein A is unsubstituted alkynylenyl.

Embodiment 7 relates to the compound of Embodiments 1-5, wherein A is unsubstituted arylenyl or heterocyclyl and X$^2$ is H.

Embodiment 8 relates to the compound of Embodiments 1-5, wherein X$^2$ is sulfonic acid or a heterocycle.

Embodiment 9 relates to the compound of Embodiment 8, wherein the heterocyclyl is 5- or 6-membered heterocycle.

Embodiment 10 relates to the compound of Embodiment 9, wherein the 6-membered heterocycle is a piperidinyl, piperazinyl or a morpholinyl group.

Embodiment 11 relates to the compound of Embodiments 1-5, wherein X$^2$ is carboxylic acid or an ester.

Embodiment 12 relates to the compound of Embodiment 1, wherein:

X$^1$ is O, S or NR$^3$, wherein R$^3$ is alkyl or arylalkyl;

R$^1$ is H, substituted or unsubstituted alkyl, substituted or unsubstituted alkoxy, substituted or unsubstituted aryl, substituted or unsubstituted aryloxy or halo; R$^2$ is H, substituted or unsubstituted alkyl, substituted or unsubstituted alkoxy, substituted or unsubstituted aryl, substituted or unsubstituted aryloxy or halo;

A is arylenyl or alkynylenyl, each of which can be substituted or unsubstituted; and X$^2$ is carboxylic acid or an ester.

Embodiment 13 relates to a compound of Embodiment 1 having the formula:

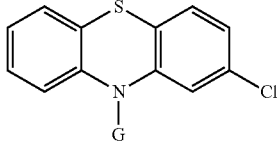

wherein G is —(CH$_2$)$_3$CH(CH$_3$)$_2$, —(CH$_2$)$_4$SO$_3$H, —(CH$_2$)$_3$SO$_3$H, —(CH$_2$)C≡CCO$_2$H,

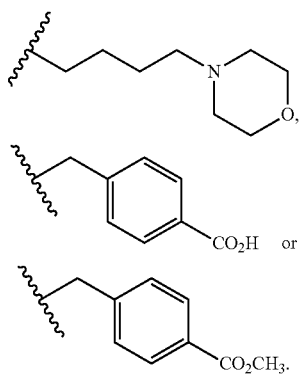

Embodiment 14 relates to a pharmaceutical composition comprising a compound of Embodiments 1-13 and a pharmaceutically acceptable excipient.

Embodiment 15 relates to a method for method for reducing the accumulation of intrinsically disordered proteins (IDPs), in a subject, the method comprising administering a therapeutically effective amount of one or more compounds of Embodiments 1-14 to a patient in need thereof.

Embodiment 16 relates to the method of Embodiment 15, wherein the IDP is at least one of α-synuclein, tau, SOD1, polyQ, oxidatively damaged proteins, c-Fos, c-Myc, and the BCL-2 family of disordered proteins.

Embodiment 17 relates to a method for treating a neurodegenerative disease comprising administering an effective amount of a compound of the formula (I) according to Embodiments 1-14 to a subject in need thereof Embodiment 18 relates to the method of Embodiment 17, wherein the neurogenerative disease is Parkinson's disease (PD), Alzheimer's disease (AD), Huntington's disease (HD) or amyotrophic lateral sclerosis (ALS, Lou Gehrig's disease).

Embodiment 19 relates to a method for treating cancer comprising administering an effective amount of a compound of the formula (I) according to Embodiments 1-14 to a subject in need thereof.

Embodiment 20 relates to the method of Embodiment 19, wherein the cancer is myeloid leukemia, glioblastoma, melanoma, breast cancer, colon cancer, cervical cancer, small-cell lung carcinoma or osteosarcoma.

Embodiment 21 relates to a method for treating a neurodegenerative disease comprising administering an effective amount of a compound of the formula (I) to a subject in need thereof:

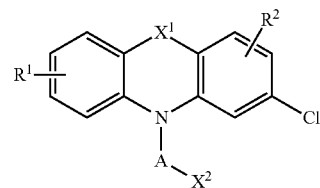

wherein X$^1$ is O, S or NR$^3$, wherein R$^3$ is alkyl or arylalkyl; R$^1$ is H, substituted or unsubstituted alkyl, substituted or unsubstituted alkoxy, substituted or unsubstituted aryl, substituted or unsubstituted aryloxy or halo;
R$^2$ is H, substituted or unsubstituted alkyl, substituted or unsubstituted alkoxy, substituted or unsubstituted aryl, substituted or unsubstituted aryloxy or halo;
A is alkylenyl, arylenyl, alkenylenyl or alkynylenyl, each of which can be substituted or unsubstituted; and
X$^2$ is H, sulfonic acid, sulfonate, carboxylic acid, ester, amide or a heterocycle.

Embodiment 22 relates to the method of Embodiment 21, wherein the neurogenerative disease is Parkinson's disease (PD), Alzheimer's disease (AD), Huntington's disease (HD) or amyotrophic lateral sclerosis (ALS, Lou Gehrig's disease).

Embodiment 23 relates the method of Embodiment 21, wherein
X$^1$ is S.

Embodiment 24 relates to the method of Embodiments 21-23, wherein R$^1$ and R$^2$ are each H.

Embodiment 25 relates to the method of Embodiments 21-24, wherein A is unsubstituted alkyl.

Embodiment 26 relates to the method of Embodiments 21-24, wherein A is unsubstituted alkynylenyl.

Embodiment 27 relates to the method of Embodiments 21-24, wherein A is unsubstituted arylenyl or heterocyclyl.

Embodiment 28 relates to the method of Embodiments 21-27, wherein X$^2$ is H.

Embodiment 29 relates to the method of Embodiments 21-27, wherein X$^2$ is sulfonic acid or a heterocycle.

Embodiment 30 relates to the method of Embodiments 21-27, wherein X$^2$ is carboxylic acid or an ester.

Embodiment 31 relates to a compound of the formula (I):

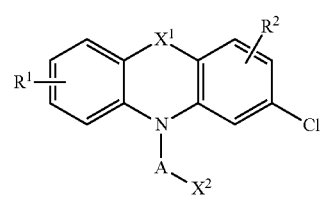

wherein X$^1$ is O, S or NR$^3$, wherein R$^3$ is alkyl or arylalkyl; R$^1$ is H, substituted or unsubstituted alkyl, substituted or unsubstituted alkoxy, substituted or unsubstituted aryl, substituted or unsubstituted aryloxy or halo;
R$^2$ is H, substituted or unsubstituted alkyl, substituted or unsubstituted alkoxy, substituted or unsubstituted aryl, substituted or unsubstituted aryloxy or halo;
A is arylenyl or alkynylenyl, each of which can be substituted or unsubstituted; and
X$^2$ is carboxylic acid or an ester.

Embodiment 32 relates to a pharmaceutical composition comprising a compound of Embodiment 31 and a pharmaceutically acceptable excipient.

What is claimed is:

1. A compound of formula (I):

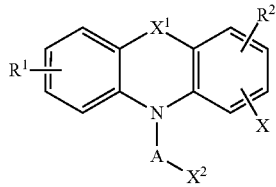

wherein:
A is alkylenyl;
$R^1$ is H;
$R^2$ is H;
X is Cl;
$X^1$ is —S—; and
$X^2$ is $S(O)_2OH$.

2. The compound of claim 1, wherein the compound is selected from the group consisting of:

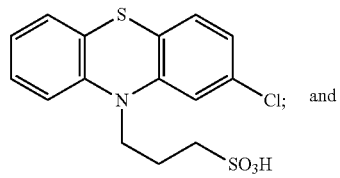

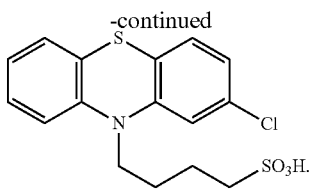

3. A pharmaceutical composition comprising a compound of claim 1 and a pharmaceutically acceptable excipient.

4. A method for reducing the accumulation of intrinsically disordered proteins in a subject, wherein the method comprises administering to the subject in need thereof a therapeutically effective amount of a compound of formula (I): wherein:
A is alkylenyl;
$R^1$ is H;
$R^2$ is H;
X is Cl;
$X^1$ is —S—; and
$X^2$ is $S(O)_2OH$.

5. The method of claim 4, wherein the intrinsically disordered protein is selected from the group consisting of B-cell lymphoma 2, c-Fos, c-Mys, an oxidatively damaged protein, polyglutamine, superoxide dismutase 1, alpha-synuclein, and tau.

6. The method of claim 4, wherein the subject has a neurodegenerative disease.

7. The method of claim 6, wherein the neurodegenerative disease is selected from the group consisting of Alzheimer's disease, amyotrophic lateral sclerosis, Huntington's disease, and Parkinson's disease.

8. The method of claim 4, wherein the subject has cancer.

9. The method of claim 8, wherein the cancer is selected from the group consisting of breast cancer, cervical cancer, colon cancer, glioblastoma, melanoma, myeloid leukemia, osteosarcoma, and small-cell lung carcinoma.

* * * * *